(12) United States Patent  
Suzuki

(10) Patent No.: US 9,330,338 B2  
(45) Date of Patent: May 3, 2016

(54) IMAGE ANALYSIS METHOD AND IMAGE ANALYSIS DEVICE

(71) Applicant: OLYMPUS CORPORATION, Tokyo (JP)

(72) Inventor: Akemi Suzuki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 409 days.

(21) Appl. No.: 13/870,711

(22) Filed: Apr. 25, 2013

(65) Prior Publication Data

US 2013/0236061 A1    Sep. 12, 2013

Related U.S. Application Data

(63) Continuation of application No. PCT/JP2010/069367, filed on Oct. 29, 2010.

(51) Int. Cl.  
*G06T 5/50* (2006.01)  
*G01N 21/64* (2006.01)  
(Continued)

(52) U.S. Cl.  
CPC ............. *G06K 9/6202* (2013.01); *G01J 3/4406* (2013.01); *G01N 21/6408* (2013.01); *G01N 21/6458* (2013.01); *G02B 21/008* (2013.01); *G02B 21/0076* (2013.01); *G06K 9/0014* (2013.01); *G06T 7/0012* (2013.01); *G01N 2021/6419* (2013.01); *G01N 2021/6421* (2013.01); *G06T 2207/10056* (2013.01); *G06T 2207/10064* (2013.01); *G06T 2207/30024* (2013.01)

(58) Field of Classification Search  
CPC .................... G06T 5/50; G06T 7/0012; G06T 2207/20216; G06T 2207/10064; G06T 2207/20224; G01N 21/6408; G01N 21/6458; G06K 9/00147

USPC .......................... 382/128, 133, 224, 228, 236  
See application file for complete search history.

(56) References Cited

U.S. PATENT DOCUMENTS

2009/0010551 A1* 1/2009 Matsuda ...................... 382/228  
2009/0238435 A1* 9/2009 Shields ......................... 382/133  
(Continued)

FOREIGN PATENT DOCUMENTS

JP    2004-108892    4/2004  
JP    2004-354348    12/2004  
(Continued)

OTHER PUBLICATIONS

Digman et al. "Measuring Fast Dynamics in Solutions and Cells with a Laser Scanning Microscope." Biophysical Journal. 89. (2005): 1317-1327. Print.*

(Continued)

*Primary Examiner* — Michael A Newman  
(74) *Attorney, Agent, or Firm* — Kenyon & Kenyon LLP

(57) ABSTRACT

An image analysis method includes acquiring fluorescent images of frames in time-series. Each fluorescent image comprises pixels in which pixel data are acquired in the time-series. The method further includes setting analysis areas to the fluorescent images, selecting the fluorescent images of two or more frames to be used in analysis, extracting data pairs each comprising two pixels in which acquisition time intervals are the same in the analysis area of each of the selected fluorescent images, and performing product sum calculation of each of the data pairs for all of the selected images to calculate a correlation value.

16 Claims, 9 Drawing Sheets

(51) Int. Cl.
- *G06T 7/00* (2006.01)
- *G06K 9/00* (2006.01)
- *G01J 3/28* (2006.01)
- *G06K 9/62* (2006.01)
- *G02B 21/00* (2006.01)
- *G01J 3/44* (2006.01)

(56) References Cited

U.S. PATENT DOCUMENTS

| | | | | |
|---|---|---|---|---|
| 2010/0272358 A1* | 10/2010 | Kanda | | 382/173 |
| 2011/0025880 A1* | 2/2011 | Nandy | | 348/226.1 |

FOREIGN PATENT DOCUMENTS

| | | |
|---|---|---|
| JP | 2005-291762 | 10/2005 |
| JP | 2005-337920 | 12/2005 |
| JP | 2006-078377 | 3/2006 |
| JP | 2007-093277 | 4/2007 |
| JP | 2010-217104 | 9/2010 |
| JP | 2010-217761 | 9/2010 |
| JP | 2010-237116 | 10/2010 |
| JP | 2011-017677 | 1/2011 |
| WO | WO 2007/037253 | 4/2007 |
| WO | WO 2008/087869 | 7/2008 |
| WO | 2011/046212 | 4/2011 |

OTHER PUBLICATIONS

Gratton, "Fluorescence correlation spectroscopy and fluorescence cross-correlation spectroscopy." Wiley Interdiscip Rev Sys Bio Med. 1.2 (2009): 1-15. Print.*

Bacia, et al. "Fluorescence Cross-correlation Spectroscopy in Living Cells." Nature Methods 3.2 (2006): 83-89. Print.*

Wiseman, et al. "Two-photon Image Correlation Spectroscopy and Image Cross-correlation Spectroscopy." Journal of Microscopy 200.1 (2000): 14-25. Print.*

Benedict, et al. "Spatiotemporal Image Correlation Spectroscopy (STICS) Theory, Verification, and Application to Protein Velocity Mapping in Living CHO Cells." Biophysical Journal 88 (2005): 3601-614. Print.*

Digman, Et Al. "Detecting Protein Complexes in Living Cells from Laser Scanning Confocal Image Sequences by the Cross Correlation Raster Image Spectroscopy." Biophysical Journal 96 (2009): 707-16. Print.*

Japanese Office Action, mailed Aug. 20, 2013, issued in corresponding Japanese Patent Application No. 2009-163992.

International Preliminary Report on Patentability, mailed May 23, 2013, issued in corresponding International Application No. PCT/JP2010/069367.

Chinese Office Action, dated Jun. 3, 2015, issued in corresponding Chinese Patent Application No. 201080069870.4.

M. Digman, et al., "Measuring Fast Dynamics in Solutions and Cells with a Laser Scanning Microscope," Biophysical Journal 89: 1317-1327 (Aug. 2005).

M. Digman, et al., "Fluctuation Correlation Spectroscopy with a Laser-Scanning Microscope: Exploiting the Hidden Time Structure," Biophysical Journal: Biophysical Letters, L33-L36 (2005).

International Search Report, dated Feb. 8, 2011, issued in corresponding International Application No. PCT/JP2010/069367.

Chinese Third Office Action, dated Dec. 4, 2015, issued in corresponding Chinese Patent Application No. 201080069870.4.

E. Gielen, et al., "Diffusion of Myelin Oligodendrocyte Glycoprotein in Living OLN-93 Cells Investigated by Raster-Scanning Image Correlation Spectroscopy (RICS)", Journal of Fluorescence 18(5): 813-819, 2008.

K. Weisshart, "Fluctuations as a Source of Information in Laser Scanning Microscopy", FCS/RICS, p. 1-31, Jun. 9, 2009.

M. Digman, et al., "Paxillin Dynamics Measured During Adhesion Assembly and Disassembly by Correlation Spectroscopy", Biophysical Journal 94(7): 2819-2831, 2008.

D. Jameson, et al., "Fluorescence Fluctuation Spectroscopy: Ushering in a New Age of Enlightenment for Cellular Dynamics", Biophysical Reviews 1(3): 105-118, 2009.

European Supplementary Search Report, dated Jan. 5, 2016, issued in corresponding European Patent Application No. 10858967.2.

* cited by examiner

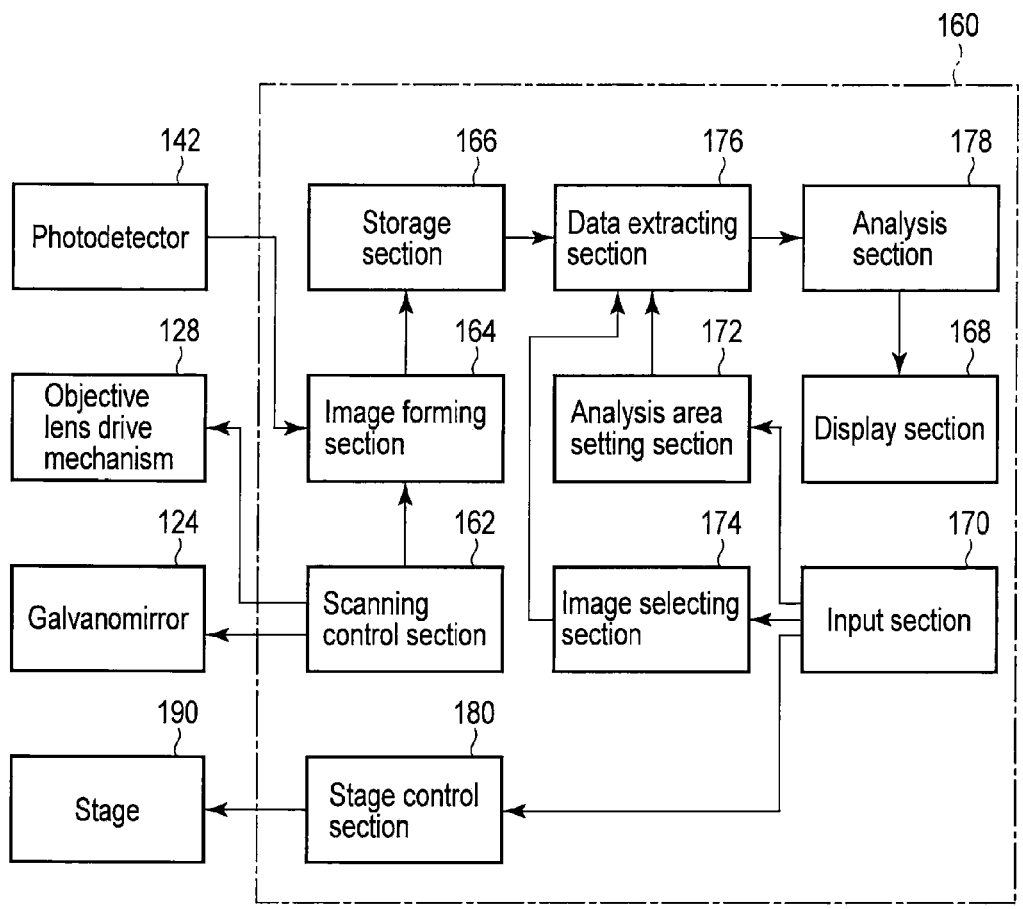
F I G. 2

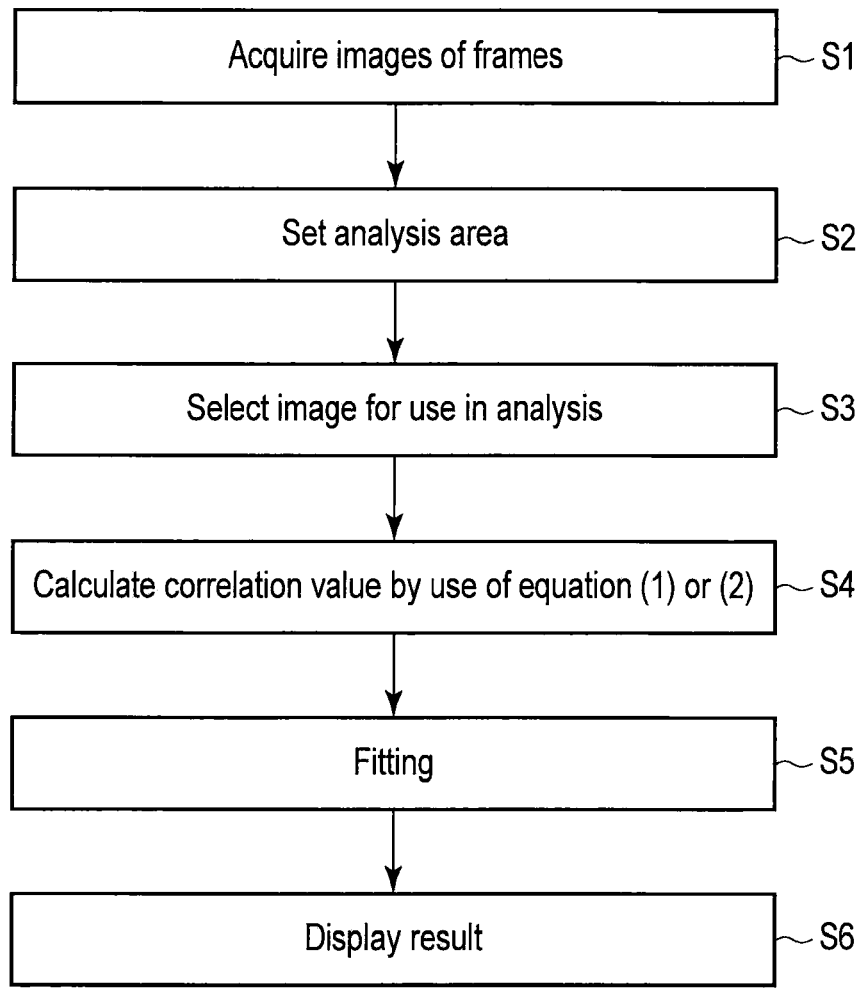
F I G. 3

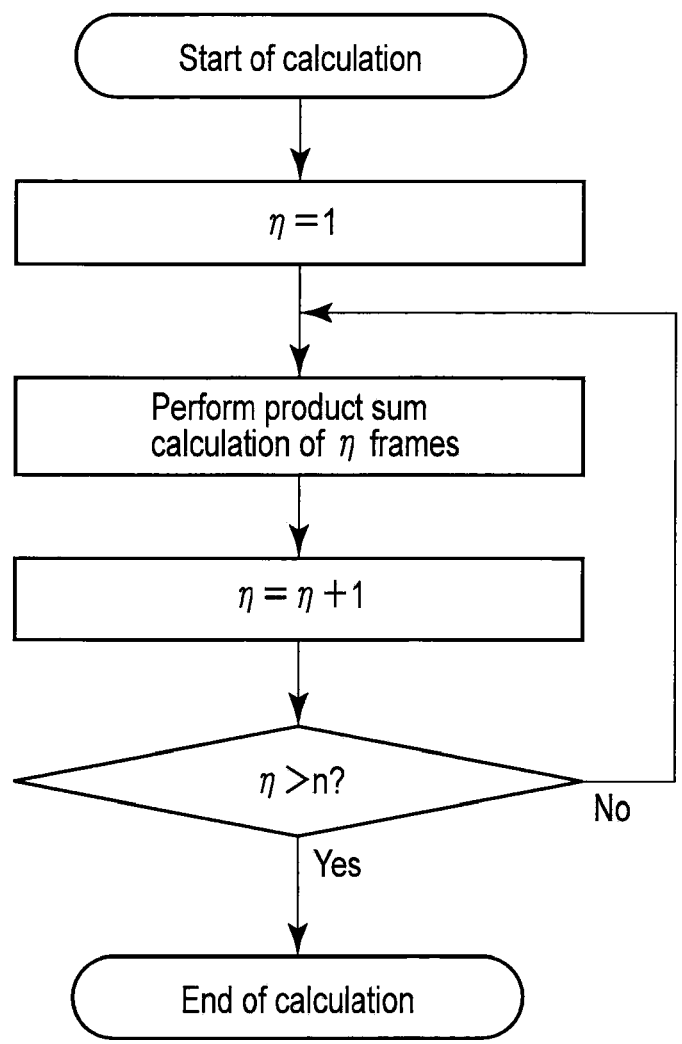
F I G. 4

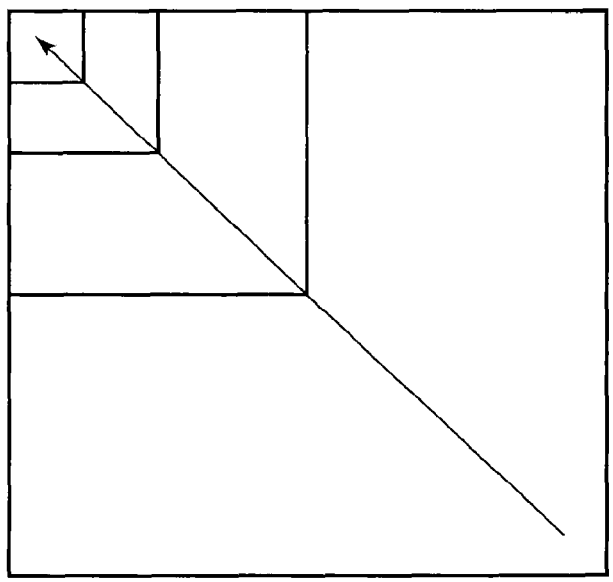
F I G. 12

IMAGE ANALYSIS METHOD AND IMAGE ANALYSIS DEVICE

CROSS-REFERENCE TO RELATED APPLICATIONS

This application is a Continuation Application of PCT Application No. PCT/JP2010/069367, filed Oct. 29, 2010.

BACKGROUND OF THE INVENTION

1. Field of the Invention

The present invention relates to an image analysis method and an image analysis device.

2. Description of the Related Art

Heretofore, as a raster image correlation spectroscopy (RICS), such methods as shown in Non-Patent Literatures 1 and 2 have been suggested. Each of these image analysis methods acquires a fluorescent image comprising raster-scanned images of one or more frames. That is, for a sample to be subjected to image analysis, an interesting area is determined, and this area is repeatedly scanned in a raster scanning system to acquire an image comprising fluorescence intensities of the frames. The fluorescence intensities in the frames are represented as data per pixel unit.

These data per pixel unit (pixel data) are different in acquisition times and acquisition positions, and hence the acquisition times and acquisition positions corresponding to the data deviate from each other.

Therefore, when space correlation analysis is performed by use of these pixel data, correlation characteristics due to fluctuation of molecules can be acquired. Then, from the correlation characteristics of the molecules, diffusion constants and numbers of the molecules can be obtained.

As understood from the above, when the space correlation analysis is performed, molecule diffusion times, the numbers of the molecules and the like can be evaluated, and hence it is possible to observe interaction between the molecules.

PRIOR ART DOCUMENT

Non-Patent Documents

Non-Patent Document 1: "Measuring Fast Dynamics in Solutions and Cells with a Laser Scanning Microscope", Michelle A. Digman, Claire M. Brown, Parijat Sengupta, Paul W. Wiseman, Alan R, Horwitz, and Enrico Gratton, Biophysical Journal, Vol. 89, P 1317 to 1327, August 2005.

Non-Patent Document 2: "Fluctuation Correlation Spectroscopy with a Laser-Scanning Microscope: Exploiting the Hidden Time Structure", Michelle A. Digman, Parijat Sengupta, Paul W. Wiseman, Claire M. Brown, Alan R. Horwitz, and Enrico Gratton, Biophysical Journal: Biophysical Letters, L33 to 36, 2005.

SUMMARY OF THE INVENTION

Technical Problem

Heretofore, to obtain one RICS analysis result in space correlation analysis of the RICS, pixel data constituting an image of one frame has only been used. This also applies to a case where the images of one or more frames are acquired, and to obtain the one RICS analysis result, the pixel data constituting the image of the one frame is only used. That is, the one RICS analysis result is not obtained by using pixel data constituting one image and pixel data constituting another image.

However, when the analysis of the RICS is performed limiting analysis areas to different local analysis areas such as nuclei, membranes, or cytoplasm of cells as in cell observation, the number of the pixels included in each analysis area is small (the number of the pixels is, e.g., 8×8). When the space correlation analysis is performed for such areas, the number of data to be used in the space correlation analysis of the RICS is excessively small, and hence there occurs the problem that accuracy of analysis results deteriorates. This problem is because space correlating calculation of the RICS is a type of statistic calculation, and hence the larger the number of the data is, the higher the accuracy becomes, and the smaller the number of the data is, the larger an error becomes. That is, when the number of the data included in the area to be subjected to the space correlation analysis is excessively small, the accuracy of the RICS analysis as the result of the statistic calculation deteriorates.

An object of the present invention is to provide an image analysis method of RICS capable of performing space correlation analysis with high accuracy even for an analysis area where the number of pixels is small.

Solution to Problem

An image analysis method according to the present invention comprises an image acquiring step of acquiring, in time-series, images of frames comprising pixels in which pixel data of the respective images are acquired in the time-series; an analysis area setting step of setting analysis areas to the images; an image selecting step of selecting, from the images, the images of two or more frames to be used in analysis; and a calculation step of extracting data pairs each comprising two pixels in which acquisition time intervals are the same in the analysis area of each of the selected images, and performing product sum calculation of each of the data pairs for all of the selected images to calculate a correlation value.

Advantageous Effects of the Invention

According to the present invention, there is provided an image analysis method of RICS capable of performing space correlation analysis with high accuracy even for an analysis area where the number of pixels is small.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 shows function blocks of a controller shown in FIG. 1;

FIG. 3 is a flowchart of image analysis according to the embodiment of the present invention;

FIG. 4 shows a calculation procedure in step 4 of the flowchart of FIG. 3;

FIG. 12 shows a result obtained by comparing diffusion constants (D) of an EGFP solution while changing an ROI size of the analysis area.

DESCRIPTION OF EMBODIMENTS

Hereinafter, embodiments of the present invention will be described with reference to the drawings.

Figure 1:
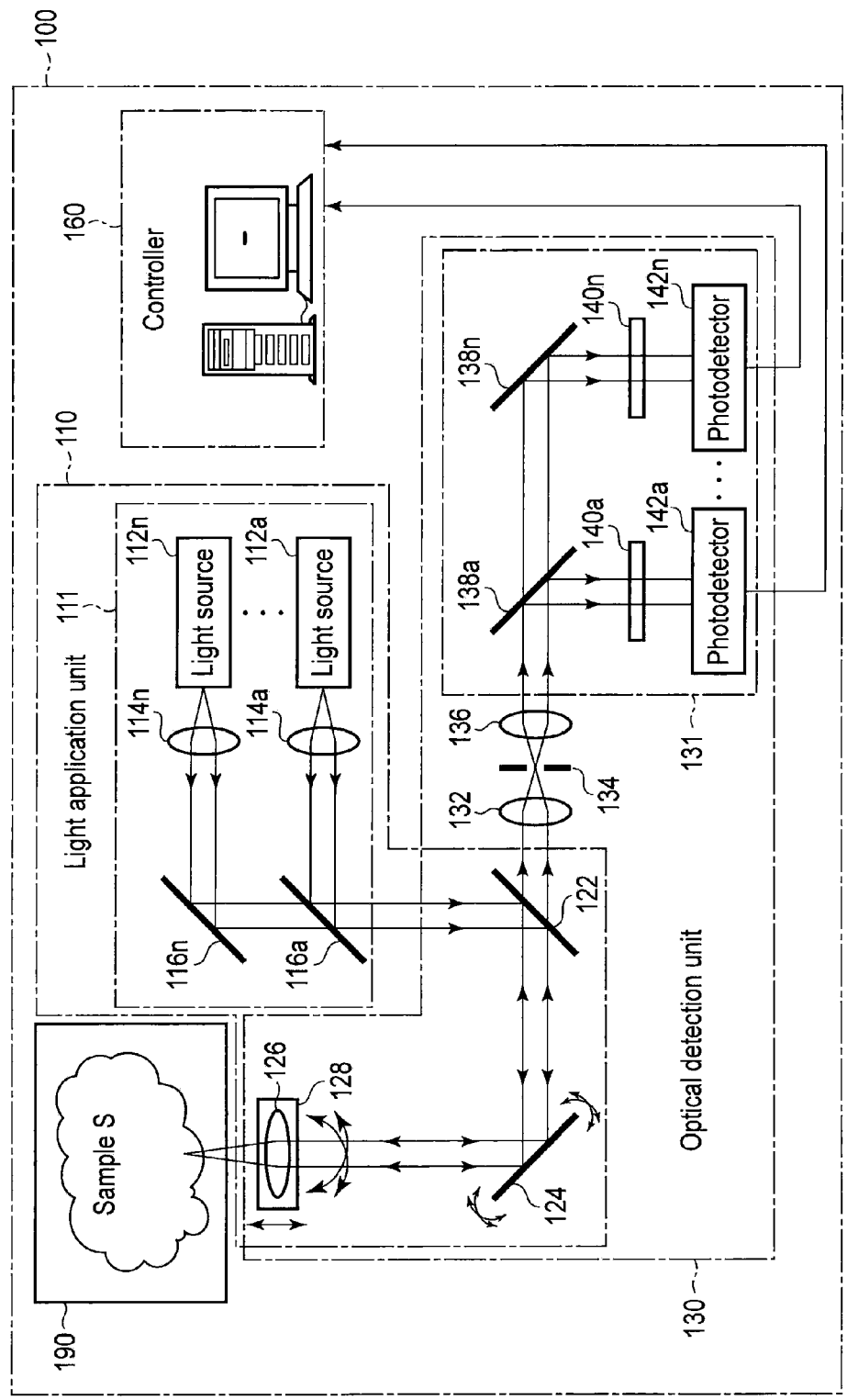
FIG. 1 schematically shows an image analysis device according to an embodiment of the present invention.

FIG. 1 schematically shows an image analysis device according to the embodiment of the present invention. This image analysis device is constituted on the basis of a scanning type confocal optical microscope for fluorescence observation of a sample.

As shown in FIG. 1, an image analysis device 100 has a light application unit 110 to apply an excitation light to a sample S, an optical detection unit 130 to detect light emitted from a point of measurement in the sample S, a controller 160 to execute control required for image analysis, and a sample stage 190 to support the sample S.

The sample S is contained in a sample container such as a micro plate or a slide glass, and mounted on the sample stage 190. The sample stage 190 supports, for example, the sample S so that the sample is movable to the light application unit 110 and the optical detection unit 130 in a lateral direction (the xy direction) and a height direction (the z direction). For example, the sample stage 190 includes three stepping motors in which output shafts are perpendicular to one another, so as to move the sample S in the xyz-direction by these stepping motors.

The image analysis device 100 is a multiplex light application/multiplex light detection type. Therefore, the light application unit 110 includes a light source system 111 of n channels, and in accordance with this system, the optical detection unit 130 includes a detection system 131 of the n channels. The detection system 131 of the n channels detects fluorescence light generated by the excitation light emitted from the light source system 111 of the n channels, respectively. Here, the n channels comprises channel 1, channel 2, . . . , and channel n. The channels vary in accordance with types of the excitation light, respectively.

The n-channel light source system 111 of the light application unit 110 includes light sources 112a, . . . , 112n, collimating lenses 114a, . . . , 114n, and dichroic mirrors 116a, . . . , 116n. The light sources 112a, 112n emit the excitation light for exciting fluorescent dyestuffs included in the sample S to cause it to emit the light (the fluorescence light) from the sample S. Wavelengths of the excitation light emitted from the light sources 112a, . . . , 112n are different from one another in accordance with types of the fluorescent dyestuffs included in the sample S. The light sources 112a, . . . , 112n comprise, for example, laser light sources of oscillation wavelengths that match the fluorescent dyestuffs in the sample S. The collimating lenses 114a, . . . , 114n collimate the excitation light emitted from the light sources 112a, . . . , 112n, respectively. The dichroic mirrors 116a, . . . , 116n reflect the excitation light that has passed through the collimating lenses 114a, . . . , 114n in the same direction, respectively. The dichroic mirrors 116a, . . . , 116n transmit the excitation light incoming from the upper side of FIG. 1, and reflect the excitation light incoming from the right side of FIG. 1, respectively. As a result, the excitation light of the different wavelengths emitted from the light sources 112a, . . . , 112n, respectively, pass through the dichroic mirror 116a and are then combined into a beam. Since the dichroic mirror 116n does not need to transmit the excitation light, it may be replaced with a simple mirror.

The light application unit 110 further includes a dichroic mirror 122, a galvanomirror 124, an objective lens 126 and an objective lens drive mechanism 128. The dichroic mirror 122 reflects the excitation light from the light source system 111 toward the galvanomirror 124, and transmits the fluorescence light emitted from the sample S. The galvanomirror 124 reflects the excitation light toward the objective lens 126, and changes a reflecting direction of the excitation light. The objective lens 126 converges the excitation light to apply it to the point of measurement in the sample S, and takes in the light from the point of measurement in the sample S. In the objective lens 126, a lens having a large NA (numerical aperture) is used for formation of a micro confocal area (the point of measurement). A size of the confocal area obtained by this lens is a diameter of about 0.6 μm and a length of about 2 μm of a substantially cylindrical area. The galvanomirror 124 constitutes xy scanning means for scanning the point of measurement in the xy direction. The xy scanning means is constituted by using a galvanomirror, but may be constituted by using an acoustooptic modulation element (AOM), a polygon mirror, a hologram scanner or the like. The objective lens drive mechanism 128 moves the objective lens 126 along an optical axis. In consequence, the point of measurement is moved in the z direction. That is, the objective lens drive mechanism 128 constitutes z scanning means for scanning the point of measurement in the z direction.

The optical detection unit 130 shares the objective lens 126, the galvanomirror 124 and the dichroic mirror 122 with the light application unit 110. The optical detection unit 130 further includes a converging lens 132, a pinhole 134 and a collimating lens 136. The converging lens 132 converges the light transmitted through the dichroic mirror 122. The pinhole 134 is disposed at a focal point of the converging lens 132. That is, the pinhole 134 is at a position that is conjugate with the point of measurement in the sample S, and selectively transmits the only light from the point of measurement. The collimating lens 136 collimates the light that has passed through the pinhole 134. The light that has passed through the collimating lens 136 enters the detection system 131 of the n channels.

The detection system 131 of the n channels includes dichroic mirrors 138a, . . . , 138n, fluorescence filters 140a, . . . , 140n, and photodetectors 142a, . . . , 142n.

The dichroic mirrors 138a, . . . , 138n selectively reflect the light of wavelengths near a wavelength region of the fluorescence light that is generated from the sample S by the excitation light from the light sources 112a, . . . , 112n, respectively. The dichroic mirror 138n does not need to transmit the light, and hence may be replaced with a simple mirror. The fluorescence filters 140a, . . . , 140n interrupt the light of undesirable wavelength components from the light reflected by the dichroic mirrors 138a, . . . , 138n, respectively, and selectively transmit the only fluorescence light generated by the excitation light from the light sources 112a, . . . , 112n. The fluorescence light transmitted through the fluorescence filters 140a, . . . , 140n enter the photodetectors 142a, . . . , 142n, respectively. The photodetectors 142a, . . . , 142n output signals corresponding to intensities of the incident light. That is, the photodetectors 142a, . . . , 142n output fluorescence intensity signals from the point of measurement in the sample S.

The controller 160 is constituted of, for example, a personal computer. The controller 160 acquires, stores and displays a fluorescent image of an observation area of the sample S, waits for input of setting of the number of frames (the frame number) of the fluorescent image to be acquired, or an analysis area, and performs the image analysis (the calculation of a correlation value), estimation of a diffusion time, and the like. Moreover, the controller 160 executes control of the galvanomirror 124, which is the xy scanning means, the objective lens drive mechanism 128, which is the z scanning means, the sample stage 190 and the like.

Function blocks of the controller shown in FIG. 1 are shown in FIG. 2. As shown in FIG. 2, the controller 160 includes a scanning control section 162, an image forming section 164, a storage section 166, a display section 168, an input section 170, an analysis area setting section 172, an image selecting section 174, a data extracting section 176, an analysis section 178 and a stage control section 180. Here, the scanning control section 162, the image forming section 164, the storage section 166, and the stage control section 180, as well as the galvanomirror 124, the objective lens drive mechanism 128, the sample stage 190, and the photodetectors 142 described above constitute an image acquisition unit, and the data extracting section 176 and the analysis section 178 constitute an operation unit.

The scanning control section 162 controls the galvanomirror 124 so that an application position of the excitation light is raster-scanned with respect to the sample S, when the fluorescent image of the sample S is acquired. Moreover, if necessary, the scanning control section 162 controls the objective lens drive mechanism 128 so that the application position of the excitation light is z-scanned with respect to the sample S. The image forming section 164 forms the fluorescent image of the sample S from information of the application position of the excitation light, which is input from the scanning control section 162, and the output signals of the photodetectors 142a, . . . , 142n. In consequence, the fluorescent image is acquired. The storage section 166 successively stores the fluorescent images formed by the image forming section 164. The display section 168 displays the fluorescent image of the sample S, or the analysis result. The input section 170 includes, for example, a mouse, and a keyboard, and cooperates with the display section 168 to constitute a GUI. This GUI is used in setting of the number of the frames to be acquired, the observation area or the analysis area, or the like. The stage control section 180 controls the sample stage 190 in accordance with input information from the input section 170 to set, for example, the observation area. The analysis area setting section 172 sets the analysis area in accordance with the input information from the input section 170. The image selecting section 174 selects the fluorescent images of two or more frames to be used in the analysis, in accordance with the input information from the input section 170. The data extracting section 176 extracts necessary data from the fluorescent image stored in the storage section 166 on the basis of the input information from the analysis area setting section 172 and the image selecting section 174. The necessary data are data pairs each comprising two pixels in which an acquisition time interval in the analysis area of each of the fluorescent images selected by the image selecting section 174 is the same. The data included in these data pairs may be, for example, all the pixel data of all the fluorescent images stored in the storage section 166 or part of the pixel data, or the data may be all the pixel data or part of the pixel data of part of the fluorescent images stored in the storage section 166. The analysis section 178 calculates the correlation values of the data extracted by the data extracting section 176 as described later.

In FIG. 1, the excitation light emitted from the light sources 112a, . . . , 112n passes through the collimating lenses 114a, . . . , 114n, the dichroic mirrors 116a, . . . , 116n, the dichroic mirror 122, the galvanomirror 124, and the objective lens 126, to be applied to the point of measurement in the sample S. The point of measurement at which the excitation light is applied is raster-scanned in the xy direction by the galvanomirror 124. Furthermore, if necessary, the point of measurement is z-scanned by the objective lens drive mechanism 128. The sample S that has received the excitation light emits the fluorescence light from the point of measurement. The light from the sample S (including an undesirable reflected light and the like in addition to the fluorescence light) reach the pinhole 134 through the objective lens 126, the galvanomirror 124, the dichroic mirror 122, and the converging lens 132. Since the pinhole 134 is at the position that is conjugate with the point of measurement, the only light from the point of measurement in the sample S passes through the pinhole 134. The light that has passed through the pinhole 134, i.e., the light from the point of measurement in the sample S enters the detection system 131 of the n channels through the collimating lens 136. The light that has entered the detection system 131 of the n channels are separated (i.e., diffracted) in accordance with the wavelengths by the dichroic mirrors 138a, 138n, and the undesirable components are removed by the fluorescence filters 140a, . . . , 140n. As a result, the only fluorescence light generated by the excitation light from the light sources 112a, . . . , 112n enters the photodetectors 142a, . . . , 142n, respectively. The photodetectors 142a, . . . , 142n output the fluorescence intensity signals indicating intensities of the incident light, i.e., the fluorescence light emitted from the point of measurement in the sample S, respectively. The fluorescence intensity signals are input into the image forming section 164. The image forming section 164 processes the input fluorescence intensity signal synchronously with positional information of the xy direction (and the z direction) every raster scanning (and z scanning) time, to form the fluorescent image of one frame of a focal plane (a flat plane or a curved plane to which the point of measurement has moved) in the sample S. The formed fluorescent image is stored in the storage section 166. A series of operations mentioned herein are repeated as much as the set number of the frames to be acquired, and the fluorescent images corresponding to the set number of the frames are acquired. The respective fluorescent images comprise the pixels in which the pixel data are acquired in time-series.

The fluorescent images stored in the storage section 166 are processed as required, and displayed in the display section 168. For example, it is possible that the fluorescent images of the frames are acquired while changing the z position of the point of measurement, and then synthesized to form a three-dimensional image, which is displayed in the display section 168.

Hereinafter, a procedure of the image analysis will be described with reference to FIG. 3 and FIG. 4. Moreover, the respective steps will be described suitably with reference to FIG. 5 to FIG. 7.

<Step S1>:

The observation area of the sample S and the number of the frames of the fluorescent images to be acquired are set. The fluorescent images of the set number of the frames of the set observation area are acquired in time-series. The acquisition of the fluorescent images is performed on the same observation area by the same scanning method. That is, when scanning after the light is emitted toward a predetermined direction until the light is again emitted toward the predetermined direction is one set of scanning, at least two or more sets of the scanning of the analysis area are performed.

Figure 5:
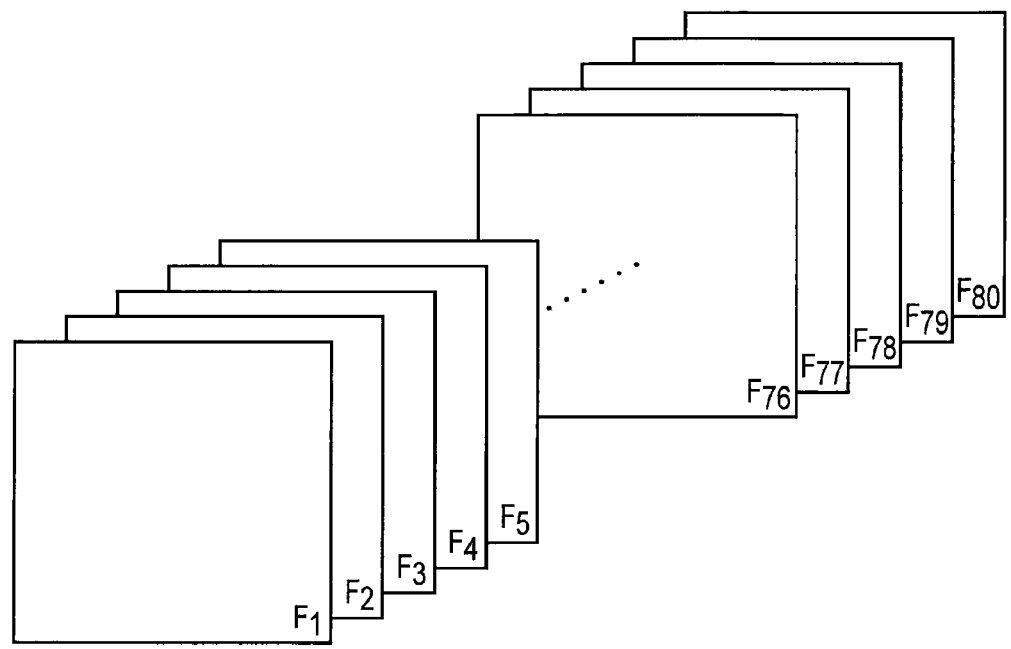
FIG. 5 shows fluorescent images of frames acquired in time-series.

The acquired fluorescent images of the frames are schematically shown in FIG. 5. In FIG. 5, $F_k$ indicates the fluorescent image of the k-th frame in one channel. In each fluorescent image, the pixel data comprise pixels acquired in time-series. The pixel data is, for example, a fluorescence intensity obtained from a two-dimensional or three-dimensional observation area.

Figure 6:
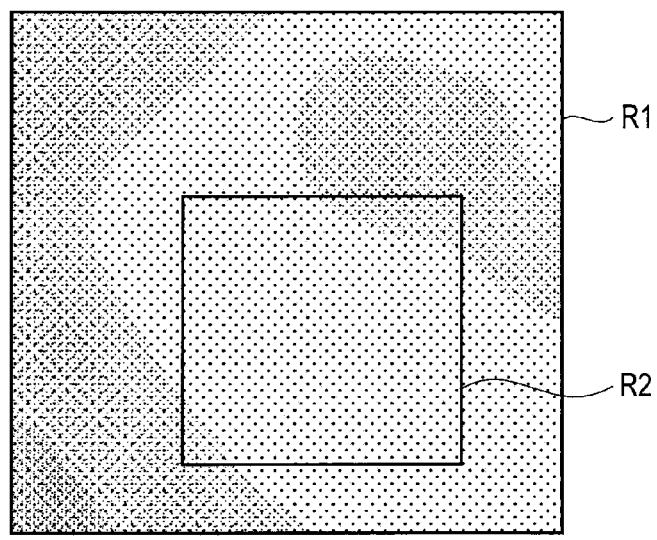
FIG. 6 shows an observation area and an analysis area.

<Step S2>:

As shown in FIG. 6, an area to be analyzed (the analysis area) R2 is set to an area (the observation area) R1 of the acquired fluorescent image. The analysis area R2 is not limited to a part of the observation area R1, and may coincide with the observation area R1. The analysis area R2 is set to the observation area R1, i.e., the scanned area in the step S1, by default in an application. When the whole observation area R1 is analyzed, this step is not required.

<Step S3>:

The fluorescent images of two or more frames to be used in the analysis are selected. The fluorescent images to be selected may be all the fluorescent images acquired in the step S1, or part of the fluorescent images acquired in the step S1. Moreover, part of the fluorescent images acquired in the step S1 may be continuous in time-series, or may not be continuous in time-series.

<Step S4>:

From the pixel data in the analysis area R2 of each of the fluorescent images selected in the step S3, the data pairs in which the acquisition time intervals are the same are extracted. Then, product sum calculation of each of the data pairs is performed for all of the selected fluorescent images to calculate the correlation value. Each of the data pairs to be extracted may be the pixel data itself corresponding to the data pair, or a statistic value of data of pixels including the pixel corresponding to the data pair. The pixels may be, for example, the pixel of attention and the pixel adjacent to the pixel of attention. The statistic value may be, for example, one of an average value, a maximum value, a minimum value, a relative difference, an absolute difference, and a relative ratio of the pixel data. Which statistic value to be used is determined by judging which information is to be obtained by the analysis of the RICS.

Moreover, in the calculation of the correlation value, each of the images may be reconstituted on the basis of the pixel data, and the correlation value of the reconstituted images may be calculated. For example, the data of the adjacent pixels are added up, to set the number of the pixel data to half. Alternatively, one pixel datum is divided into a plurality of data. Under normal circumstances, once the image is acquired, the number of the pixel data does not increase. However, it is supposed that an intensity of the acquired pixel data spreads around the pixel data in Gaussian distribution, to compensate for the pixel data that cannot originally be acquired. The number of the pixel data essentially does not increase, but visual effects improve.

In the calculation of the correlation value, for example, a space auto-correlation value is calculated by using the following Equation (1):

$$G_{sa}(\xi, \psi) = \frac{\sum_{\eta=1}^{n} \sum I_\eta(x, y) * I_\eta(x+\xi, y+\psi)/M_{11}}{\left(\sum_{\eta=1}^{n} (\sum I_\eta(x, y)/M_\eta)/n\right)^2} \quad (1)$$

where $G_{sa}$ is the space auto-correlation value of the RICS, n is the number of the frames to be used in the calculation, $\eta$ is a parameter to specify the frame ($\eta$=1, 2, ..., n), $I\eta$ is the pixel data of the $\eta$-th frame, x and y are spatial coordinates of the point of measurement, $\xi$ and $\psi$ are variations of the spatial coordinates from the point of measurement, $M_{11}$ is the number of data product sum calculation times, and $M_\eta$ is the total number of the data of the $\eta$-th frame. The number n of the frames to be used in the calculation is represented by an integer that is two or more and not more than the number of the frames of the acquired fluorescent images.

Alternatively, in the calculation of the correlation value, for example, a space cross-correlation value is calculated by using the following Equation (2):

$$G_{sc}(\xi, \psi) = \frac{\sum_{\eta=1}^{n} \sum I_{1\eta}(x, y) * I_{2\eta}(x+\xi, y+\psi)/M_{12}}{\left(\sum_{\eta=1}^{n} (\sum I_{1\eta}(x, y)/M_{1\eta})/n\right)\left(\sum_{\eta=1}^{n} (\sum I_{2\eta}(x, y)/M_{2\eta})/n\right)} \quad (2)$$

where $G_{sc}$ is the space cross-correlation value of the RICS, n is the number of the frames to be used in the calculation, $\eta$ is the parameter to specify the frame ($\eta$=1, 2, ..., n), $I_{1\eta}$ is fluorescence intensity data of the $\eta$-th frame of the channel 1, $I_{2\eta}$ is fluorescence intensity data of the $\eta$-th frame of the channel 2, x and y are spatial coordinates of the point of measurement, $\xi$ and $\psi$ are variations of the spatial coordinates from the point of measurement, $M_{12}$ is the number of data product sum calculation times, $M_{1\eta}$ is the total number of the data of the $\eta$-th frame of the channel 1, and $M_{2\eta}$ is the total number of the data of the $\eta$-th frame of the channel 2. The Equation (2) is a calculating equation of the space cross-correlation value between the channel 1 and the channel 2, but the channels may suitably be changed. The number n of the frames to be used in the calculation is represented by an integer that is two or more and not more than the number of the frames of the acquired fluorescent images.

Figure 7:
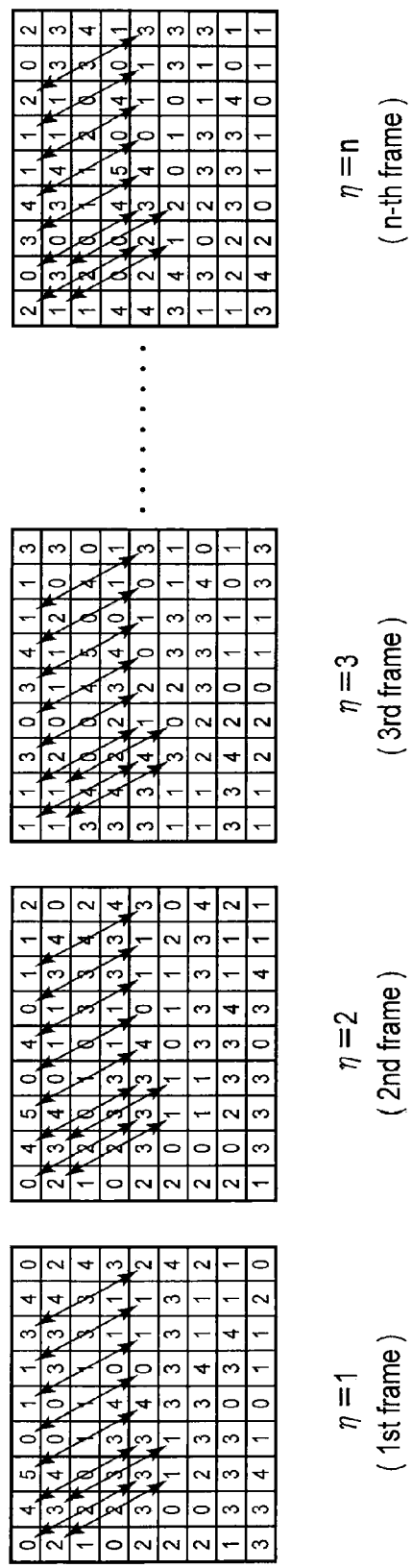
FIG. 7 schematically shows a product sum calculation part of a space correlating calculation for the fluorescent images of the frames classified into groups.

Here, a procedure of the calculation in accordance with the Equation (1) or the Equation (2) will be described with reference to FIG. 4 and FIG. 7. FIG. 7 schematically shows the product sum calculation in $G_s(2, 4)$.

First, $\eta$=1 is set, and the product sum calculation of the data pair of two pixels having a space deviation (2, 4) is performed on the analysis area of the fluorescent image of the first frame. It is to be noted that in the analysis of the RICS, the analysis area is repeatedly scanned by a raster scanning system, and hence the data pair of two pixels having the space deviation (2, 4) means the data pair in which an interval between the times when the data are acquired is a predetermined time.

Next, 1 is added to $\eta$, $\eta$=2 is set, and the product sum calculation of the data pair of two pixels having a space deviation (2, 4) is continuously performed on the analysis area of the fluorescent image of the second frame.

Afterward, as long as a value obtained by adding 1 to η is not more than n, the product sum calculation of the data pair of two pixels having the space deviation (2, 4) is continuously performed on the analysis area of the fluorescent image of the η-th frame.

Finally, the product sum calculation is continuously performed for all of the analysis areas of the fluorescent images of the n frames in this way to calculate the correlation value.

Thus, in the present embodiment, instead of performing the product sum calculation of the data pair at η=1 and then obtaining one correlation analysis result only on the basis of the result of the product sum calculation, the product sum calculation of the data pairs is performed when η is from 1 to n, and then one correlation analysis result is obtained on the basis of the results of these product sum calculations.

Moreover, in other words, all the combinations of data of any two pixels in which an interval between times when the light is applied is a predetermined time are extracted from the respective pixel data obtained by n sets of scanning, and one correlation analysis result is obtained concerning all the extracted data combinations.

<Step S5>:

Fitting of the calculation result of the space correlation value of the above step S4 is performed in accordance with the following Equation (3):

$$G_s(\xi, \psi) = S(\xi, \psi) * G(\xi, \psi) \quad (3)$$

$$S(\xi, \psi) = \exp\left(-\frac{\frac{1}{2}*\left[\left(\frac{2\xi\delta_r}{W_0}\right)^2 + \left(\frac{2\psi\delta_r}{W_0}\right)^2\right]}{\left(1 + \frac{4D(\tau_p\xi + \tau_l\psi)}{W_0^2}\right)}\right)$$

$$G(\xi, \psi) = \frac{\gamma}{N}\left(\left(1 + \frac{4D(\tau_p\xi + \tau_l\psi)}{W_0^2}\right)^{-1} * \left(1 + \frac{4D(\tau_p\xi + \tau_l\psi)}{W_Z^2}\right)^{-1/2}\right)$$

where $G_s$ is the space correlation value of the RICS, S is an influence of the scanning in the analysis of the RICS, G is an influence of time delay in the analysis of the RICS, D is a diffusion constant, ξ and ψ are the variations of the spatial coordinates from the point of measurement, $\delta_r$ is a pixel size, N is the number of molecules, $W_0$ is a radius of an excitation laser beam in a lateral direction, $W_Z$ is a radius of the excitation laser beam in a vertical direction, $\tau_p$ is a pixel time, $\tau_l$ is a line time, and γ is an arbitrary constant.

It is to be noted that γ can suitably be set in accordance with the system. For example, the fitting may be performed by using γ=1.

Moreover, the pixel time means a deviation in acquisition time between the pixels. Moreover, the line time means a deviation in acquisition time between the first pixel of any line and the first pixel of the next line. That is, the line time means the time required to scan one line.

The fitting is performed in this way by use of the Equation (3), to estimate the diffusion time. Specifically, the correlation value $G_{sa}$ or the correlation value $G_{sc}$ to different delay times is obtained by using the Equation (1) or the Equation (2). Here, the delay time means a difference between the acquisition time of one pixel and the acquisition time of another pixel. For example, the delay time between (ξ, ψ)=(1, 1) and (ξ, ψr)=(4, 2) is represented by $(4-1)\tau_p+(2-1)\tau_p$.

Here, in the Equation (3), when the delay time is zero, (ξ=0, ψ=0), S is 1, and $G_s$ is represented by 1/N. Therefore, the number of the molecules can be obtained. This is newly substituted into the Equation (3).

Then, the suitable diffusion constant D and the suitable number N of the molecules are obtained by causing a difference between the correlation value $G_{sa}$ or the correlation value $G_{sc}$ obtained as the measured value and $G_s$ obtained as a theoretical value to be minimum while varying the diffusion constant D and the number N of the molecules, which are unknown values. Consequently, the fitting in accordance with the Equation (3) is to estimate the most suitable molecule number or diffusion constant in the two-dimensional or three-dimensional observation area while varying the diffusion constant D and the number N of the molecules.

Then, the diffusion time can be obtained from the diffusion constant.

That is, a relation between the diffusion constant and the diffusion time is represented by the following Equation (4):

$$\tau = W_0^2/4D \quad (4)$$

where D means the diffusion constant, τ means the diffusion time, and $W_0$ means the radius of the excitation laser beam in the lateral direction.

Figure 8:
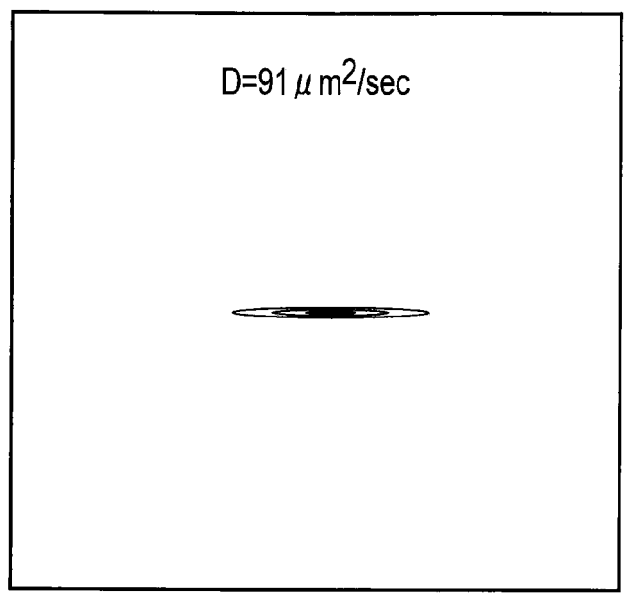
FIG. 8 is an image in which a calculation result of a space correlation value by RICS to small molecules is represented by a luminance.
Figure 9:
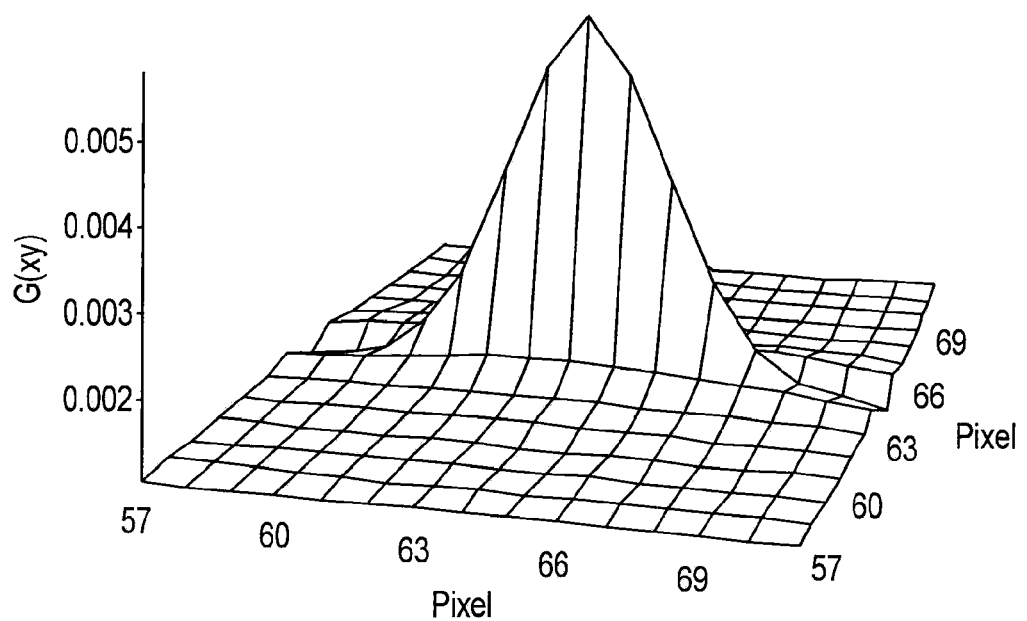
FIG. 9 shows a fitting result of the space correlation value by the RICS to the small molecules.
Figure 10:
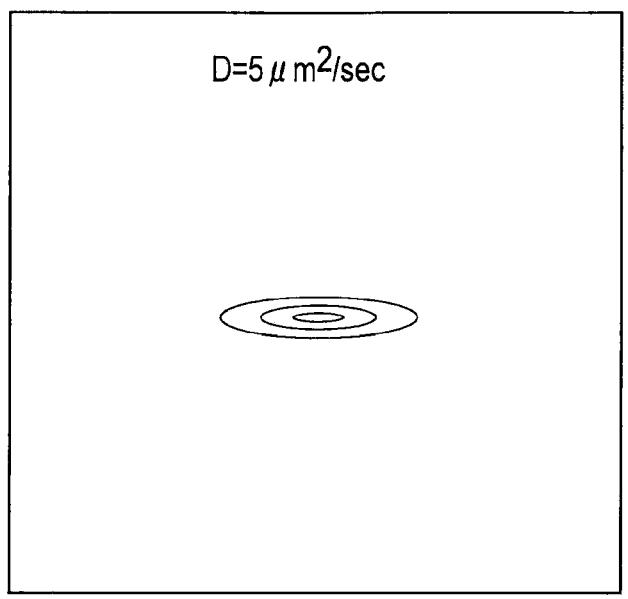
FIG. 10 is an image in which a calculation result of a space correlation value by the RICS to large molecules is represented by the luminance.
Figure 11:
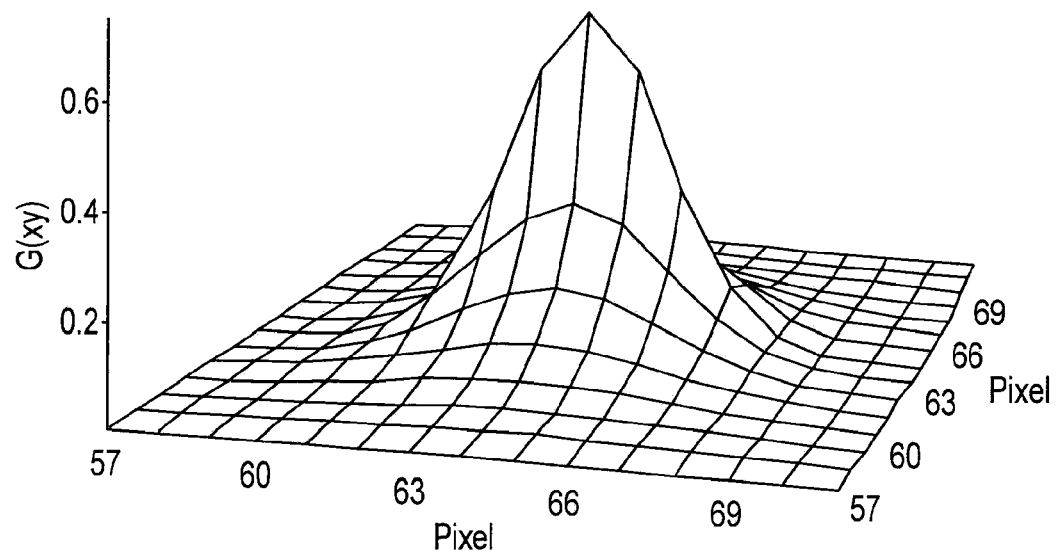
FIG. 11 shows a fitting result of the space correlation value by the RICS to the large molecules.

<Step S6>:

The analysis result is displayed and suitably stored. Specifically, the calculation result of the space correlation value obtained in the step S4 and the fitting result of the space correlation value obtained in the step S5 are displayed. An example of the analysis result is shown in FIG. 8 to FIG. 11. FIG. 8 is an image in which the calculation result of the space correlation value to small molecules is represented by a luminance, and FIG. 9 shows a fitting result of the image. Moreover, FIG. 10 is an image in which the calculation result of the space correlation value to large molecules is represented by the luminance, and FIG. 11 shows a fitting result of the image.

Heretofore, in the spatial correlation analysis in which such image data as in the RICS is used as a calculation base, one correlation value is calculated by using pixel data in an analysis area of an image of one frame. When the analysis area becomes small, the number of data pairs that can be used in product sum calculation decreases. Therefore, when the analysis area becomes very small, the correlation value cannot suitably be calculated. FIG. 12 shows a result obtained by comparing diffusion constants (D) of an EGFP solution (obtained by diluting a dyestuff liquid with distilled water) while changing an ROI size of the analysis area. In FIG. 12, the ROI size=256 means that 256×256 pixels are included in the analysis area. As seen from FIG. 12, when the ROI size of the analysis area increases, a value closer to a diffusion constant 90 (the theoretical value) of the EGFP solution is indicated, and when the ROI size of the analysis area decreases, a value farther from the diffusion constant 90 (the theoretical value) of the EGFP solution is indicated. That is, it is seen that when the pixel data increase, a value (the measured value) closer to a correct result (the theoretical value) can be obtained.

On the other hand, according to the present embodiment, in spatial correlation analysis in which such image data as in the RICS is used as a calculation base, one correlation value is not calculated by the product sum calculation of two pixels in the analysis area of the image of one frame, but the product sum calculation of two pixels in the analysis area of the image of each of the frames is continuously performed to calculate one correlation value. Therefore, the data to be used in the calculation of the one correlation value is not limited to data in the image of the one frame, and the number of the frames of the images to be used in the calculation of the one correlation value is increased. As a result, the number of the data to be used in the calculation of the correlation value increases. Therefore, the analysis of the RICS can be performed with high accuracy.

As above, the embodiments of the present invention have been described with reference to the drawings, but the present invention is not limited to these embodiments, and various modifications and alterations may be made without departing from the scope of the present invention.

Moreover, in the embodiments, the image acquired by the raster scanning has been described, but the image is not limited to the image acquired by the raster scanning, and may be an image comprising pixels in which pixel data are acquired in time-series, or an image acquired by another scanning method.

REFERENCE SIGNS LIST

100 . . . image analysis device, 110 . . . light application unit, 112a, . . . , 112n . . . light source, 114a, . . . , 114n . . . collimating lens, 116a, . . . , 116n . . . dichroic mirror, 122 . . . dichroic mirror, 124 . . . galvanomirror, 126 . . . objective lens, 128 . . . objective lens drive mechanism, 130 . . . optical detection unit, 132 . . . converging lens, 134 . . . pinhole, 136 . . . collimating lens, 138a, . . . , 138n . . . dichroic mirror, 140a, . . . , 140n . . . fluorescence filter, 142a, . . . , 142n . . . photodetector, 160 . . . controller, 162 . . . scanning control section, 164 . . . image forming section, 166 . . . storage section, 168 . . . display section, 170 . . . input section, 172 . . . analysis area setting section, 174 . . . image selecting section, 176 . . . data extracting section, 178 . . . analysis section, 180 . . . stage control section, 190 . . . sample stage, R1 . . . observation area, and R2 . . . analysis area.

What is claimed is:

1. An image analysis method comprising:
an image acquiring step of acquiring, in time-series, images of frames comprising pixels in which pixel data of the respective images are acquired in the time-series;
an analysis area setting step of setting analysis areas to the images;
an image selecting step of selecting, from the images, the images of two or more frames to be used in analysis; and
a calculation step of extracting data pairs each comprising two pixels in which acquisition time intervals are the same in the analysis area of each of the selected images, and performing product sum calculation of each of the data pairs for all of the selected images to calculate a correlation value,
wherein the calculation step performs auto-correlating or cross-correlating calculation of a two-dimensional or three-dimensional observation area by use of the following Equation (1) or the following Equation (2):

$$G_{sa}(\xi, \psi) = \frac{\sum_{\eta=1}^{n} \sum I_\eta(x, y) * I_\eta(x+\xi, y+\psi)/M_{11}}{\left(\sum_{\eta=1}^{n} (\sum I_\eta(x, y)/M_\eta)/n\right)^2} \quad (1)$$

where $G_{sa}$ is a space auto-correlation value of RICS, n is the number of the frames to be used in the calculation, $\eta$ is a parameter to specify the frame ($\eta=1, 2, \ldots, n$), $I\eta$ is the pixel data for $\eta$-th frame, x and y are spatial coordinates of a point of measurement, $\xi$ and $\psi$ are variations of the spatial coordinates from the point of measurement, $M_{11}$ is the number of data product sum calculation times, $M_\eta$ is the total number of the data of the $\eta$-th frame, and the number n of the frames to be used in the calculation is represented by an integer that is two or more and not more than the number of frames of acquired fluorescent images, $$G_{sc}(\xi, \psi) = \frac{\sum_{\eta=1}^{n} \sum I_{1\eta}(x, y) * I_{2\eta}(x+\xi, y+\psi)/M_{12}}{\left(\sum_{\eta=1}^{n} (\sum I_{1\eta}(x, y)/M_{1\eta})/n\right)\left(\sum_{\eta=1}^{n} (\sum I_{2\eta}(x, y)/M_{2\eta})/n\right)} \quad (2)$$

where $G_{sc}$ is a space cross-correlation value of the RICS n is the number of the frames to be used in the calculation, $\eta$ is the parameter to specify the frame ($\eta=1, 2, \ldots, n$), $I_{1\eta}$ is fluorescence intensity data of the $\eta$-th frame of channel 1, $I_{2\eta}$ is fluorescence intensity data of the $\eta$-th frame of channel 2, x and y are spatial coordinates of the point of measurement, $\xi$ and $\psi$ are variations of the spatial coordinates from the point of measurement, $M_{12}$ is the number of data product sum calculation times, $M_{1\eta}$ is the total number of the data of the $\eta$-th frame of the channel 1, $M_{2\eta}$ is the total number of the data of the $\eta$-th frame of the channel 2, and the number n of the frames to be used in the calculation is represented by an integer that is two or more and not more that the number of frames of acquired fluorescent images.

2. The image analysis method according to claim 1, wherein the selected images comprise all the images.

3. The image analysis method according to claim 1, wherein the selected images comprise part of the images.

4. The image analysis method according to claim 1, wherein each of the data pairs is a statistic value of the pixel data, the statistic value being one of an average value, a maximum value, a minimum value, a relative difference, an absolute difference, and a relative ratio of the pixel data.

5. The image analysis method according to claim 1, wherein the pixel data are fluorescence intensities obtained from a two-dimensional or three-dimensional observation area.

6. The image analysis method according to claim 1, wherein the calculation step reconstitutes each of the images on the basis of the pixel data, and calculates the correlation value of the reconstituted images.

7. The image analysis method according to claim 1, wherein the images are obtained by a scanning type microscope.

8. The image analysis method according to claim 1, wherein the calculation step performs fitting of the calculation result of the space correlation value by use of the following Equation (3), to estimate the number of molecules and a diffusion constant:

$$G_s(\xi, \psi) = S(\xi, \psi) * G(\xi, \psi) \quad (3)$$

$$S(\xi, \psi) = \exp\left(-\frac{\frac{1}{2}*\left[\left(\frac{2\xi\delta r}{W_0}\right)^2 + \left(\frac{2\psi\delta r}{W_0}\right)^2\right]}{\left(1 + \frac{4D(\tau_p\xi + \tau_l\psi)}{W_0^2}\right)}\right)$$

$$G(\xi, \psi) = \frac{\gamma}{N}\left(\left(1 + \frac{4D(\tau_p\xi + \tau_l\psi)}{W_0^2}\right)^{-1} * \left(1 + \frac{4D(\tau_p\xi + \tau_l\psi)}{W_Z^2}\right)^{-1/2}\right)$$

where $G_s$ is the space correlation value of the RICS, S is an influence of scanning in the analysis of the RICS, G is an influence of time delay in the analysis of the RICS, D is the diffusion constant, $\xi$ and $\psi$ are the variations of the spatial coordinates from the point of measurement, $\delta_r$ is a pixel size, N is the number of the molecules, $W_0$ is a radius of an excitation laser beam in a lateral direction, $W_Z$ is a radius of the excitation laser beam in a vertical direction, $T_p$ is a pixel time, $T_l$ is a line time, and $\gamma$ is an arbitrary constant.

9. An image analysis device comprising:
image acquiring means to acquire, in time-series, images of frames comprising pixels in which pixel data of the respective images are acquired in time-series;
analysis area setting means to set analysis areas to the images;
image selecting means to select, from the images, the images of two or more frames to be used in analysis; and
calculation means to extract data pairs each comprising two pixels in which acquisition time intervals are the same in the analysis area of each of the selected images, and performing product sum calculation of each of the data pairs for all of the selected images to calculate a correlation value,
wherein the calculation means performs auto-correlating or cross-correlating calculation of a two-dimensional or three-dimensional observation area by use of the following Equation (1) or the following Equation (2):

$$G_{sa}(\xi, \psi) = \frac{\sum_{\eta=1}^{n} \sum I_\eta(x, y) * I_\eta(x+\xi, y+\psi)/M_{11}}{\left(\sum_{\eta=1}^{n} (\sum I_\eta(x, y)/M_\eta)/n\right)^2} \quad (1)$$

where $G_{sa}$ is a space auto-correlation value of RICS, n is the number of the frames to be used in the calculation, $\eta$ is a parameter to specify the frame ($\eta=1, 2, \ldots, n$), I$\eta$ is the pixel data for $\eta$-th frame, x and y are spatial coordinates of a point of measurement, $\xi$ and $\psi$ are variations of the spatial coordinates from the point of measurement, $M_{11}$ is the number of data product sum calculation times, $M_\eta$ is the total number of the data of the $\eta$-th frame, and the number n of the frames to be used in the calculation is represented by an integer that is two or more and not more than the number of frames of acquired fluorescent images, $$G_{sc}(\xi, \psi) = \frac{\sum_{\eta=1}^{n} \sum I_{1\eta}(x, y) * I_{2\eta}(x+\xi, y+\psi)/M_{12}}{\left(\sum_{\eta=1}^{n} (\sum I_{1\eta}(x, y)/M_{1\eta})/n\right)\left(\sum_{\eta=1}^{n} (\sum I_{2\eta}(x, y)/M_{2\eta})/n\right)} \quad (2)$$

where $G_{sc}$ is a space cross-correlation value of the RICS, n is the number of the frames to be used in the calculation, n is the parameter to specify the frame ($\eta=1, 2, \ldots, n$), $I_{1\eta}$ is fluorescence intensity data of the $\eta$-th frame of channel 1, $I_{2\eta}$ is fluorescence intensity data of the n-th frame of channel 2, x and y are spatial coordinates of the point of measurement, $\xi$ and $\psi$ are variations of the spatial coordinates from the point of measurement, $M_{12}$ is the number of data product sum calculation times, $M_{1\eta}$ is the total number of the data of the $\eta$-th frame of the channel 1, $M_{2\eta}$ is the total number of the data of the $\eta$-th frame of the channel 2, and the number n of the frames to be used in the calculation is represented by an integer that is two or more and not more that the number of frames of acquired fluorescent images.

10. The image analysis device according to claim 9, wherein the selected images comprise all the images.

11. The image analysis device according to claim 9, wherein the selected images comprise part of the images.

12. The image analysis device according to claim 9, wherein each of the data pairs is a statistic value of the pixel data, the statistic value being one of an average value, a maximum value, a minimum value, a relative difference, an absolute difference, and a relative ratio of the pixel data.

13. The image analysis device according to claim 9, wherein the pixel data are fluorescence intensities obtained from a two-dimensional or three-dimensional observation area.

14. The image analysis device according to claim 9, wherein the calculation means reconstitutes each of the images on the basis of the pixel data, and calculates the correlation value of the reconstituted images.

15. The image analysis device according to claim 9, wherein the images are obtained by a scanning type microscope.

16. The image analysis device according to claim 9, wherein the calculation means performs fitting of the calculation result of the space correlation value by use of the following Equation (3), to estimate the number of molecules and a diffusion constant:

$$G_s(\xi, \psi) = S(\xi, \psi) * G(\xi, \psi) \quad (3)$$

$$S(\xi, \psi) = \exp\left(-\frac{\frac{1}{2} * \left[\left(\frac{2\xi\delta r}{W_0}\right)^2 + \left(\frac{2\psi\delta r}{W_0}\right)^2\right]}{\left(1 + \frac{4D(\tau_p\xi + \tau_l\psi)}{W_0^2}\right)}\right)$$

$$G(\xi, \psi) = \frac{\gamma}{N}\left(\left(1 + \frac{4D(\tau_p\xi + \tau_l\psi)}{W_0^2}\right)^{-1} * \left(1 + \frac{4D(\tau_p\xi + \tau_l\psi)}{W_Z^2}\right)^{-1/2}\right)$$

where $G_s$ is the space correlation value of the RICS, S is an influence of scanning in the analysis of the RICS, G is an influence of time delay in the analysis of the RICS, D is the diffusion constant, $\xi$ and $\psi$ are the variations of the spatial coordinates from the point of measurement, $\delta_r$ is a pixel size, N is the number of the molecules, $W_0$ is a radius of an excitation laser beam in a lateral direction, $W_Z$ is a radius of the excitation laser beam in a vertical direction, $T_p$ is a pixel time, $T_l$ is a line time, and $\gamma$ is an arbitrary constant.

* * * * *